(12) United States Patent
Boschat et al.

(10) Patent No.: US 6,518,449 B1
(45) Date of Patent: Feb. 11, 2003

(54) METHOD FOR REGENERATING A HYDROGENATION CATALYST, METHOD FOR HYDROGENATING COMPOUNDS COMPRISING NITRILE FUNCTIONS

(75) Inventors: Vincent Boschat, Lyons (FR); Philippe Leconte, Mevzieu (FR)

(73) Assignee: Rhodia Fiber & Resin Intermediates, Courbevoie Cedex (FR)

( * ) Notice: Subject to any disclaimer, the term of this patent is extended or adjusted under 35 U.S.C. 154(b) by 0 days.

(21) Appl. No.: 09/582,657

(22) PCT Filed: Dec. 23, 1998

(86) PCT No.: PCT/FR98/02856

§ 371 (c)(1),
(2), (4) Date: Feb. 9, 2001

(87) PCT Pub. No.: WO99/33561

PCT Pub. Date: Jul. 8, 1999

(30) Foreign Application Priority Data

Dec. 29, 1997 (FR) .............................................. 97 16832

(51) Int. Cl.$^7$ ................................................ B01J 25/04
(52) U.S. Cl. ....................................... 558/459; 502/301
(58) Field of Search ........................... 558/459; 502/301

(56) References Cited

U.S. PATENT DOCUMENTS 2,604,455 A * 7/1952 Reynolds et al.

FOREIGN PATENT DOCUMENTS

| DE | 832604 | * | 7/1949 |
| FR | 2211287 | * | 7/1974 |
| GB | 833592 | * | 4/1960 |

* cited by examiner

Primary Examiner—Joseph K. McKane
Assistant Examiner—Rebecca Anderson
(74) Attorney, Agent, or Firm—Burns, Doane, Swecker & Mathis, L.L.P.

(57) ABSTRACT

The invention concerns a method for regenerating a hydrogenation catalyst, and hydrogenation methods carried out with a catalyst comprising at least one regenerated catalyst. More particularly, it concerns a method for regenerating Raney catalysts used in total or partial hydrogenating processes of compounds comprising nitrile functions into amine functions. Said method consists in treating the spent catalyst with a basic solution and optionally in subjecting said catalyst to hydrogenation before stripping to eliminate the impurities present on the catalyst. Thus, the regenerating method enables to recuperate up to 100% of the catalytic activity.

14 Claims, No Drawings

METHOD FOR REGENERATING A HYDROGENATION CATALYST, METHOD FOR HYDROGENATING COMPOUNDS COMPRISING NITRILE FUNCTIONS

This is a 371 of international application PCT/FR98/02856 with filing date of Dec. 23, 1998.

The present invention relates to a process for regenerating a hydrogenation catalyst, and to hydrogenation processes carried out with a catalyst comprising at least the regenerated catalyst.

The invention relates more particularly to a process for regenerating catalysts of Raney type used in processes for the total or partial hydrogenation of compounds comprising nitrile functions into amine functions.

The hydrogenation of compounds comprising nitrile functions into amine compounds has been carried out industrially for a long time.

Thus, hexamethylenediamine, a compound used in particular for the manufacture of polyhexamethyleneadipamide, also referred to as PA66 and known as "Nylon", is manufactured industrially by hydrogenation of adiponitrile in the presence of a Raney nickel catalyst. This process is described in particular in U.S. Pat. No. 3,821,305. Other processes for hydrogenating nitrile or polynitrile compounds into amine compounds are described in U.S. Pat. Nos. 3,372,195, 2,287,219, 2,449,036, 3,565,957, 3,998,881, 4,188,146, 4,235,521, 4,254,059 and WO 95/17959.

These documents relate to the hydrogenation of various aliphatic, aromatic, substituted, unsaturated, etc. nitrile compounds.

These patents also relate to processes which are carried out in the presence of solvent, sodium hydroxide and ammonia. They are generally carried out with Raney-type catalysts such as Raney nickel or Raney cobalt.

The preparation of these Raney catalysts has been described for a long time, and in particular in U.S. Pat. No. 1,638,190 and in J.A.C.S. 54, 4116 (1932). A preparation process starting with nickel, molybdenum and aluminium alloy is described in U.S. Pat. No. 2,948,887.

Raney-type hydrogenation catalysts whose catalytic effect is improved by doping with other metal elements have also been proposed. For example, U.S. Pat. No. 4,153,578 describes a Raney nickel catalyst comprising molybdenum. This catalyst is used in particular for reducing aldehydes to alcohols.

Processes for hydrogenating polynitrile compounds by reduction of certain nitrile functions to give compounds comprising nitrile and amine functions have also been proposed. One application developed is the partial hydrogenation, known as the semi-hydrogenation, of aliphatic dinitriles such as adiponitrile into aminonitriles such as aminocapronitrile. Thus, U.S. Pat. No. 4,389,348 describes the semi-hydrogenation of dinitrile into ω-aminonitrile with hydrogen, in an aprotic solvent and ammonia medium and in the presence of rhodium deposited on a basic support. U.S. Pat. No. 5,151,543 describes the semi-hydrogenation of dinitriles into aminonitriles in a solvent in a molar excess of at least 2/1 relative to the dinitrile, comprising liquid ammonia or an alkanol containing a mineral base in the presence of a catalyst such as Raney nickel and Raney cobalt.

Similarly, patent application WO 93/16034 describes a process for the semi-hydrogenation of adiponitrile into aminocapronitrile in the presence of a Raney nickel catalyst, a base and a transition metal complex.

In the documents cited, the problem of reducing the consumption of catalyst, either by better recovery or by recycling, is not envisaged.

The recovery of the hydrogenation catalyst is envisaged in the case of complete hydrogenation by U.S. Pat. No. 4,429,159, which describes a process for pretreating Raney nickel catalyst with a carbonate to reduce the entrainment of this catalyst in the hexamethylenediamine flow. The catalyst thus recovered can be recycled after washing with water, as a mixture with fresh catalyst.

Processes for regenerating the catalysts used in semi-hydrogenation processes have also been described in patent applications WO 97/37964 and WO 97/37963. The catalysts are treated with a flow of nitrogen at a temperature of between 150° C. and 400° C., in the absence of any liquid or solvent. After regeneration by treatment with hydrogen, the catalysts are washed with water to neutral pH and optionally conditioned with liquid ammonia. These regeneration processes use a high-temperature treatment which can give rise to partial sintering of the catalyst. In addition, these processes do not make it possible to recover total catalytic activity, in particular when the process for hydrogenating the nitrile compounds is carried out in liquid medium, and more particularly in the presence of a basic compound.

One of the aims of the present invention is to propose a process for regenerating a hydrogenation catalyst of the Raney catalyst type which makes it possible to recover an activity substantially equivalent to that of a fresh catalyst.

To this end, the invention proposes a process for regenerating a catalyst of the Raney catalyst type for the total or partial hydrogenation of nitrile functions into amine functions on organic compounds, characterized in that it consists in mixing the spent catalyst, separated from the hydrogenation reaction medium, with an aqueous solution of a basic compound having an anion concentration of greater than 0.01 mol/l, in maintaining the mixture at a temperature below 130° C. and then in washing the treated catalyst with water or a basic aqueous solution until the final pH of the washing waters is between 12 and 13.

According to another preferred characteristic of the invention, the process for regenerating the catalyst can comprise a hydrogenation of this catalyst, carried out by treating the catalyst under a hydrogen atmosphere and at a temperature below 130° C.

According to the invention, the catalyst can be placed under a hydrogen atmosphere before maintaining the spent catalyst/basic solution mixture at the reaction temperature. In this case, the basic treatment and the hydrogenation of the spent catalyst are carried out simultaneously.

In another embodiment, the catalyst is hydrogenated before the step of mixing with the basic aqueous solution. Finally, it is also possible to subject the catalyst, treated with a basic solution and optionally washed, to the hydrogenation step.

From the point of view of cost-effectiveness and ease of implementation, the process consisting in simultaneously carrying out the treatment with a basic a solution and hydrogenation is preferred.

The various characteristics and definitions of the products or operating conditions described below are applicable to all the embodiments mentioned above.

The regeneration process of the invention can be carried out in batchwise or continuous mode.

The process of the invention allows a regeneration of the hydrogenation or semi-hydrogenation catalyst at low temperature, thus avoiding deterioration of the catalyst, more particularly a reduction in the doping effect of the metal elements contained in the Raney catalyst.

According to the invention, the catalysts which can be regenerated by the process described above are Raney-type catalysts such as, for example, Raney nickel and Raney cobalt. These catalysts can advantageously comprise one or more other elements, often referred to as dopants, such as, for example, chromium, titanium, molybdenum, tungsten, manganese, vanadium, zirconium, iron, zinc and more generally the elements from groups IIB, IVB, IIIB, VB, VIB, VIIB and VIII of the Periodic Table of the Elements. Among these dopant elements, chromium, iron and/or titanium or a mixture of these elements are considered as being the most advantageous and are usually present at a concentration by weight (expressed relative to the Raney nickel or Raney cobalt metal) of less than 10%, preferably less than 5%.

Raney catalysts often comprise traces of metals present in the alloy used to prepare the said catalysts. Thus, aluminium is especially present in these catalysts.

According to one preferred characteristic of the invention, the basic aqueous solution used to treat the catalyst is a solution of alkaline base or aqueous ammonia. The basic compound preferably has a high solubility in water.

Mention may be made of sodium hydroxide, potassium hydroxide, lithium hydroxide or caesium hydroxide as basic compounds that are suitable.

The concentration of anions in this basic solution is advantageously between 0.01 N and 10 N, preferably between 0.02 N and 7 N.

The concentration by weight of the catalyst in the basic solution is between 5% and 30% relative to the reaction medium.

In variants comprising a treatment with hydrogen, the reaction medium either consists of the basic solution and the catalyst as described above, or consists of the spent catalyst alone, or of the catalyst treated with the basic solution and optionally washed. The reactor is placed under a partial pressure of hydrogen advantageously of greater than $10^5$ Pa.

The reaction medium is then heated to a temperature below 130° C., preferably between 100° C. and 130° C., for a time which is determined experimentally and by precalibration of the process. This time is of the order of a few hours, advantageously between 1 hour and 10 hours.

In order to allow an exchange with the hydrogen contained in the reactor, the reaction medium is advantageously stirred. Needless to say, other processes for supplying hydrogen, such as bubbling or a packing column, may be used to carry out this treatment without departing from the invention. However, one of the advantages of the process of the invention is that it makes it possible to obtain an effective treatment with a high regeneration yield without the need for complex processes to promote the contact between the hydrogen and the catalyst.

After the catalyst has been treated with a basic solution and has optionally undergone a hydrogenation, it is either extracted from the medium or concentrated in this medium by the usual concentration or separation techniques such as, for example, filtration, decantation, centrifugation, evaporation or the like. The catalyst thus separated out or concentrated is subjected to a washing step in order partially to remove the basic solution and also all the impurities and compounds which limit the activity of the catalyst.

This washing operation can be carried out with water or with a dilute basic solution. The reason for this is that the washing operation makes it possible to remove all the impurities, but must maintain the pH of the catalyst at a value above 12, advantageously between 12 and 13. This pH is monitored by measuring the pH of the washing waters.

Thus, in one preferred embodiment, in particular when the regeneration process is carried out continuously, the washing solution is a basic solution with a concentration of between 0.01 N and 0.1 N.

The catalyst thus regenerated can be used either alone or as a mixture with fresh catalyst in processes for the hydrogenation of compounds comprising nitrile functions.

A subject of the invention is also a process for hydrogenating compounds comprising at least one nitrile function into amine compounds, for example as described in patent application WO 95/19959.

This process consists briefly in adding the nitrile compound to a reaction medium in a concentration by weight of between 0.001% and 30% relative to the total weight of the reaction medium.

The reaction medium is a liquid medium which contains at least one solvent. This reaction medium advantageously contains water in an amount preferably of less than or equal to 50%, preferentially between 0.1% and 15%, by weight.

In addition to the water, a solvent of the alcohol and/or amide type can be provided, such as methanol, ethanol, propanol, isopropanol, butanol, glycols, polyols, dimethylformamide or dimethylacetamide. When water is present, this solvent represents 2 to 4 parts by weight per part of water present.

In one preferred embodiment, the reaction medium also comprises the amine whose preparation is targeted by the hydrogenation process. Thus, in the case of the hydrogenation of adiponitrile into hexamethylenediamine, the process is carried out in the presence of hexamethylenediamine.

The concentration by weight of amine is between 50% and 99% by weight relative to the total weight of the solvent in the reaction medium.

The reaction medium advantageously comprises a basic compound when the catalyst is of the Raney type.

This base is present in a concentration of greater than 0.1 mol/kg of catalyst, preferably between 0.1 mol/kg and 10 mol/kg.

The hydrogenation reaction is carried out by maintaining a suitable pressure of hydrogen in the chamber, i.e. a pressure advantageously of between 0.10 MPa and 10 MPa, and a reaction medium temperature of less than 150° C., preferably less than or equal to 100° C.

The above process is given by way of illustration. The invention can also apply to other processes in which the hydrogenation is carried out in the presence of ammonia, for example.

A subject of the invention is also a process for semi-hydrogenating compounds comprising at least two nitrile functions, in which at least one nitrile function is reduced to an amine function.

Such processes are used in particular for the synthesis of aminonitrile compounds which, on cyclizing hydrolysis, give lactams. These lactams are monomers for the manufacture of homopolyamides.

Thus, one of the industrialized applications is the manufacture of caprolactam, which is a monomer for polyamide 6, obtained by semi-hydrogenation of adiponitrile into aminocapronitrile and cyclizing hydrolysis of this compound into caprolactam.

This process is described in particular in patent applications WO 93/16034, WO 93/12073 and U.S. Pat. No. 4,248,799. This process uses Raney nickel as catalyst.

Thus, in this process, adiponitrile is added to a reaction medium comprising an alkaline base and/or aqueous ammonia, hydrogen, a Raney nickel catalyst and a transition metal complex. The reaction medium can contain a solvent such as an alcohol.

The catalyst is either dispersed in the reaction medium or supported on a fixed bed.

In another embodiment, the Raney catalyst (nickel or cobalt) can be treated with an alkaline alkoxide, it being possible for the hydrogenation reaction to be carried out in the absence of water and in the presence of an aprotic solvent such as tetrahydrofuran, dioxane, aliphatic diamines, alcohols or ethers.

The semi-hydrogenation process can also be carried out using a Raney catalyst such as Raney nickel comprising a dopant element as defined previously.

In this process, the hydrogenation medium comprises water in a proportion of at least 0.5% by weight relative to the total amount of liquid compounds in the reaction medium, aminonitrile and/or diamine formed by the hydrogenation, and unconverted nitrile compound. The reaction medium also comprises a strong inorganic base, i.e. an alkaline hydroxide present in a concentration so from 0.1 mol/kg to 3 mol/kg of catalyst.

In these processes, the catalysts can consist of a mixture of fresh catalyst and of catalysts regenerated according to the process of the invention. It is also possible to use only a regenerated catalyst.

The nitrile compounds which can be totally or partially reduced by the processes of the invention are, by way of example, α,ω-dinitrile compounds comprising a linear or branched aliphatic chain of 1 to 12 carbon atoms, such as adiponitrile, methyl glutaronitrile, ethyl succinonitrile, malononitrile, succinonitrile, glutaronitrile or a mixture of these compounds.

In general, the catalysts which can be regenerated by the process of the invention are advantageously used in combination with a basic compound in processes for hydrogenating nitrile compounds.

Other advantages and details of the invention will emerge more clearly in the light of the examples below, which are given purely as a guide and with no limiting nature.

EXAMPLE 1

Regeneration of a Raney Ni Catalyst Used in a Process for Hydrogenating Adiponitrile (ADN) to Hexamethylenediamine (HMD)

The hydrogenation of adiponitrile (ADN) is carried out using a catalyst based on Raney nickel 50 (doped with 1.8% Cr and 1% Fe) in the presence of an alkaline hydroxide such as KOH and/or NaOH, according to the process described in patent WO 95/17959.

When the activity of the catalyst is no longer satisfactory for correct exploitation of the adiponitrile hydrogenation process, it is separated from the reaction medium in order to be regenerated according to the process of the invention. The catalyst treated in the present example has an activity equal to 30% of the activity of the fresh catalyst.

The activity of the catalysts is determined by the following standardized catalytic test:

About 1 to 2 g of Raney Ni paste is taken and washed 6 times with 50 ml of distilled water. Exactly 0.40 g of catalyst is weighed out in a pycnometer. The said catalyst is introduced into a 150 ml stainless steel autoclave equipped with a stirring system, a heating system, means for introducing hydrogen and reagents and means for measuring and monitoring the temperature and pressure. Along with the catalyst, about 0.4 g of water is also entrained (this amount is taken into account in the weight composition of the 42 g of reaction solvent composed of 90% HMD and 10% water). The HMD, the water and the potassium hydroxide (in a proportion of 0.05% by weight of the reaction mixture, i.e. 0.8 mol KOH/kg Ni) are loaded into the autoclave under an argon atmosphere. The autoclave is purged with nitrogen and hydrogen. It is then heated to 80° C. and maintained at 25 bar of hydrogen by means of a hydrogen tank. The system for recording the hydrogen pressure in the said tank is switched on and 6 g of ADN are rapidly injected. The hydrogenation is monitored up to the end of consumption of hydrogen.

The initial rate of hydrogenation obtained with the spent and regenerated catalysts are compared with that obtained with fresh Raney Ni 50, and the activity of a catalyst is given by the following formula:

$$\text{Activity of the catalyst} = \frac{\text{Initial rate with the catalyst}}{\text{Initial rate with fresh Raney Ni50}} \times 100$$

The spent catalyst above is mixed with 6 N sodium hydroxide solution in order to obtain a mixture having the following composition by mass: 18/82 Ni/6 N NaOH.

This mixture is loaded into a 500 ml round-bottomed flask and refluxed for 3 h at 105° C. with stirring.

The catalyst is then washed with water to a pH equal to about 12.5, in order to avoid precipitation of the sodium aluminates in the form of aluminium trihydroxides, so as to avoid deactivation of the catalyst during storage. The pH is monitored by measuring the pH of the washing waters.

The activity of the catalyst for the manufacture of HMD which was 30%, is equal to 90% after regeneration.

EXAMPLE 2

Regeneration of a Raney Ni Catalyst Used in a Process for Semi-hydrogenating Adiponitrile (ADN) into Aminocapronitrile (ACN)

The catalyst used in a process for semi-hydrogenating adiponitrile into aminocapronitrile carried out under the conditions described in patent WO 93/16034 is a Raney nickel which is identical to the one described in Example 1.

The spent catalyst recovered has an activity equal to 10% of that of a fresh catalyst.

This catalyst is mixed with 0.05 N sodium hydroxide solution in order to obtain a spent catalyst/liquid phase weight ratio equal to 20/80.

This mixture is introduced into a 1.3 l stainless steel autoclave equipped in a similar manner to the 150 ml machine described previously.

The reactor is pressurized to 20 bar with hydrogen, stirred at 500 rpm and heated to 120° C. A high gas/liquid transfer is not necessary given that the solubility of hydrogen under the regeneration conditions is sufficient. After 1 h at 120° C., the reactor is cooled rapidly under hydrogen and the liquid/solid mixture is removed.

The catalyst is then washed continuously with 0.05 N NaOH solution.

The activity of the catalyst before regeneration is 10%, and after regeneration this activity is equal to that of the fresh catalyst, i.e. about 100%.

EXAMPLE 3

Regeneration of a Raney Ni Catalyst Used in a Process for Hydrogenating Adiponitrile (ADN) into Hexamethylenediamine (HMD).

The spent catalyst of Example 1 was subjected to a regeneration according to the process described in Example 2, the sodium hydroxide solution having a concentration of 3 N instead of 0.05 N.

The activity of the regenerated catalyst is equal to that of the fresh catalysts

EXAMPLE 4

Regeneration of a Raney Ni Catalyst Used in a Process for Semi-hydrogenating Adiponitrile (ADN) into Aminocapronitrile (ACN) and Hexamethylenediamine The catalysts used in the process for hydrogenating adiponitrile into HMD and ACN as described in U.S. Pat. No. 5,151,543 are regenerated according to the process described in Example 2 above.

The spent catalysts are obtained from the synthesis of ACN and from the synthesis of HMD and their activity is 30% and 10%, respectively, which activity after regeneration, is equal to that of the fresh catalysts.

What is claimed is:

1. Process for regenerating catalysts of the Raney catalyst type for the total or partial hydrogenation of nitrile functions into amine functions of organic compounds, comprising mixing the spent catalyst, extracted from the reaction medium, with an aqueous solution of a basic compound having a basic ion concentration of greater than 0.01 mol/l, maintaining the mixture at a temperature below 130° C. and then washing the treated catalyst with water or a basic solution until the final pH of the washing waters is between 12 and 13.

2. Process according to claim 1, wherein basic aqueous solution is a solution of alkaline base or aqueous ammonia.

3. Process according to claim 1, wherein the basic aqueous solution is a solution of sodium hydroxide, lithium hydroxide or caesium hydroxide.

4. Process according to claim 1 wherein the washing is carried out with a sodium hydroxide solution having a concentration of between 0.01 N and 0.1 N.

5. Process according to claim 1 wherein the spent catalyst, the catalyst treated with a basic solution and optionally washed, or the spent catalyst/basic aqueous solution mixture before or after maintenance at a temperature below 130° C., is placed under a hydrogen atmosphere and brought to a temperature below 130° C.

6. Process according to claim 5, wherein the mixture containing the catalyst to be treated is stirred.

7. Process according to claim 1 wherein the regeneration process is carried out in continuous or batchwise mode.

8. Process according to claim 1, wherein the concentration by weight of spent catalyst in the catalyst/basic solution mixture is between 5% and 30% relative to the mixture.

9. Process according to claim 1, wherein the catalyst of Raney metal type comprises Raney nickel and/or Raney cobalt.

10. Process according to claim 1, wherein the Raney catalyst comprises a dopant element comprising an element from groups IIB, IVB, IIIB, VB, VIB, VIIB and/or VIII of the Periodic Table of the Elements.

11. Process according to claim 10, wherein the dopant element comprising titanium, chromium, zirconium, vanadium, molybdenum, manganese, zinc, tungsten iron.

12. Process according to claim 1 wherein the catalyst is used in combination with a basic compound in the hydrogenation reactions.

13. Process according to claim 9 wherein the compound comprising nitrile functions comprises α,ω-dinitrile compounds comprising a linear or branched aliphatic chain of 1 to 12 carbon atoms, or a mixture of these compounds.

14. The process according to claim 13, wherein said α,w-dinitrile compounds comprise adiponitrile, methyl glutaronitrile, ethyl succinonitrile, malononitrile, succinonitrile or glutaronitrile.

* * * * *